(12) United States Patent
Florence et al.

(10) Patent No.: US 7,081,495 B1
(45) Date of Patent: Jul. 25, 2006

(54) CATIONIC COMPOUNDS AND THEIR USE AS MACRO MOLECULAR CARRIERS

(75) Inventors: Alexander T Florence, London (GB); Andrew F Wilderspin, London (GB); Istvan Toth, Brisbane (AU); Henry K Bayele, London (GB); Thiagarajan Sakthivel, London (GB)

(73) Assignee: School of Pharmacy, University of London, London (GB)

( * ) Notice: Subject to any disclaimer, the term of this patent is extended or adjusted under 35 U.S.C. 154(b) by 0 days.

(21) Appl. No.: 09/786,091

(22) PCT Filed: Sep. 23, 1999

(86) PCT No.: PCT/GB99/03189

§ 371 (c)(1), (2), (4) Date: Mar. 23, 2001

(87) PCT Pub. No.: WO00/16807

PCT Pub. Date: Mar. 30, 2000

(30) Foreign Application Priority Data

Sep. 23, 1998 (EP) .................................. 98307712
Sep. 10, 1999 (GB) .................................. 9921478.5

(51) Int. Cl.
*C08G 63/685* (2006.01)
*A61K 38/04* (2006.01)

(52) U.S. Cl. ............... 525/54.1; 525/54.11; 424/192.1; 424/193.1; 424/280.1; 514/2; 514/15; 530/300; 530/332

(58) Field of Classification Search ............... 525/54.1, 525/54.11; 424/192.1, 193.1, 280.1; 514/2, 514/15; 530/300, 332
See application file for complete search history.

(56) References Cited

U.S. PATENT DOCUMENTS 6,194,543 B1 * 2/2001 Florence et al. ............ 530/300

FOREIGN PATENT DOCUMENTS

| EP | 0884327 | 12/1998 |
| WO | 94/02506 | 2/1994 |
| WO | 98/40502 | 9/1998 |

OTHER PUBLICATIONS

T. Sakthivel, et al., "Synthesis and Physiochemical Properties of Lipophilic Polyamide Dendrimers", *Chemical Abstracts*, vol. 129, No. 6, Aug. 10, 1998, Abstract No. 68022.

A.V. Kabanov, et al., "DNA Complexes With Polycations For the Delivery of Genetic Material Into Cells", *Bioconjugate Chemistry*, vol. 6, No. 1, Jan. 1, 1995, pp. 7-20.

\* cited by examiner

*Primary Examiner*—James J. Seidleok
*Assistant Examiner*—Olga Asinovsky
(74) *Attorney, Agent, or Firm*—Dickstein, Shapiro, Morin & Oshinsky, LLP.

(57) ABSTRACT

Dendrimers comprising a dentritic polypeptide with one dendron having terminal cationic groups and a lipidic anchor, preferably comprising $C_{6-24}$-alkyl group containing α-amino acyl groups, preferably joined to the focal group, are used to assist transfection of cells in vitro and in vivo by DNA. The complex of dendrimer and DNA may be used in gene therapy, for instance to delivery clotting factor genes to cells.

32 Claims, 8 Drawing Sheets

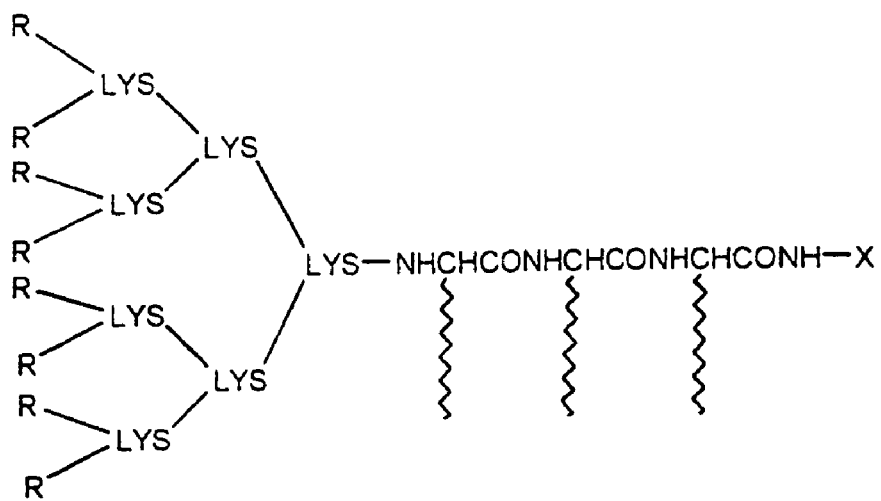
Compounds 1/3
| | | |
|---|---|---|
| 1 | R = NH$_2$ | X = - |
| 1b | R = Lys(NH$_2$)$_2$ | X = - |
| 1c | R = Lys (Lys (NH$_2$)$_2$)$_2$ | X = - |
| 1d | R = Lys(NH$_2$)$_2$ | X = GPKKKRKVG |
| 1e | R = Lys (Lys(NH$_2$)$_2$)$_2$ | X = - GPKKKRKVG |
| 3a | R = NH$_2$ | |
| 3b | R = Lys(NH$_2$)$_2$ | |
| 3c | R = Lys(Lys(NH$_2$)$_2$)$_2$ | |
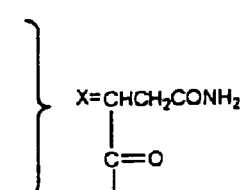
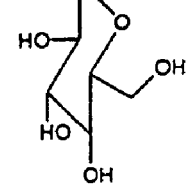
Fig. 1

Compound 2

2a    $R = NH_2$    X = -
2b    $R = Orn(NH_2)_2$    X = -
2c    $R = Orn(Orn(NH_2)_2)_2$    X = -
2d    $R = Orn(NH_2)_2$    X = GPKKKRKVG
2e    $R = Orn(Orn(NH_2)_2)_2$    X = GPKKKRKVG

Compound 4

4a    $R = NH_2$
4b    $R = Lys(NH_2)_2$
4c    $R = Lys(Lys(NH_2)_2)_2$

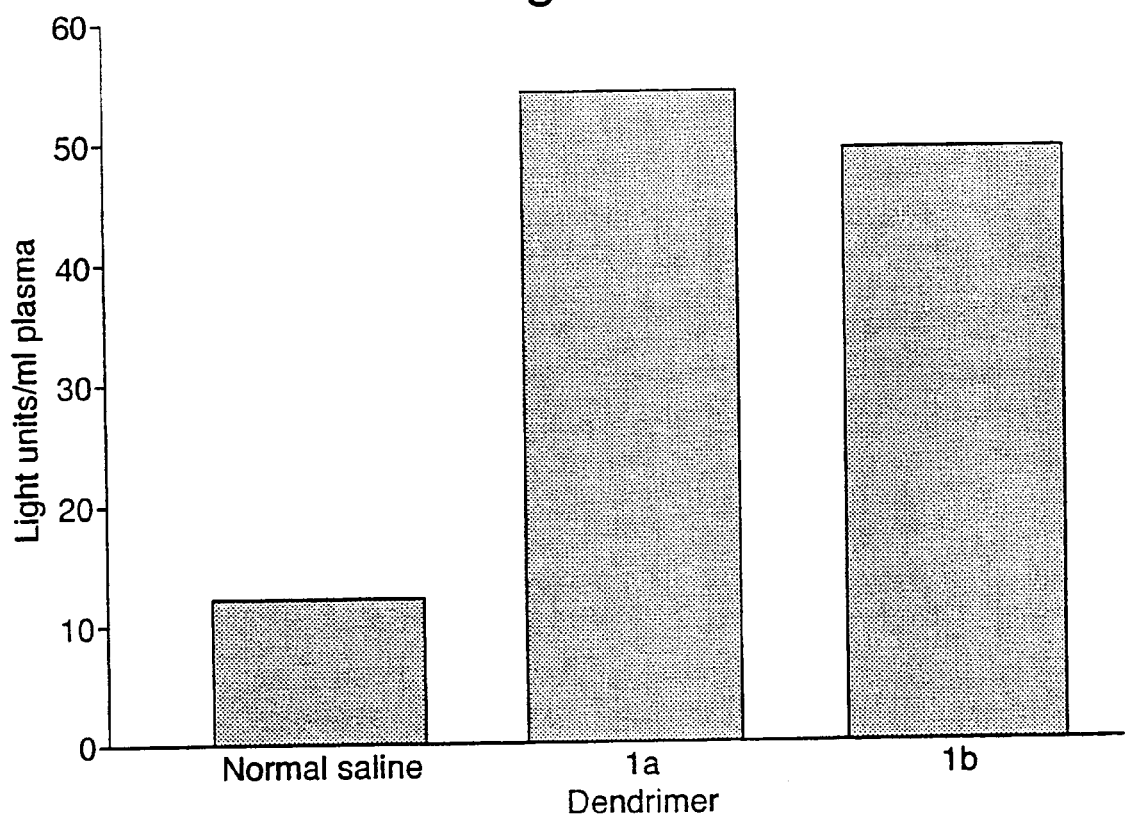

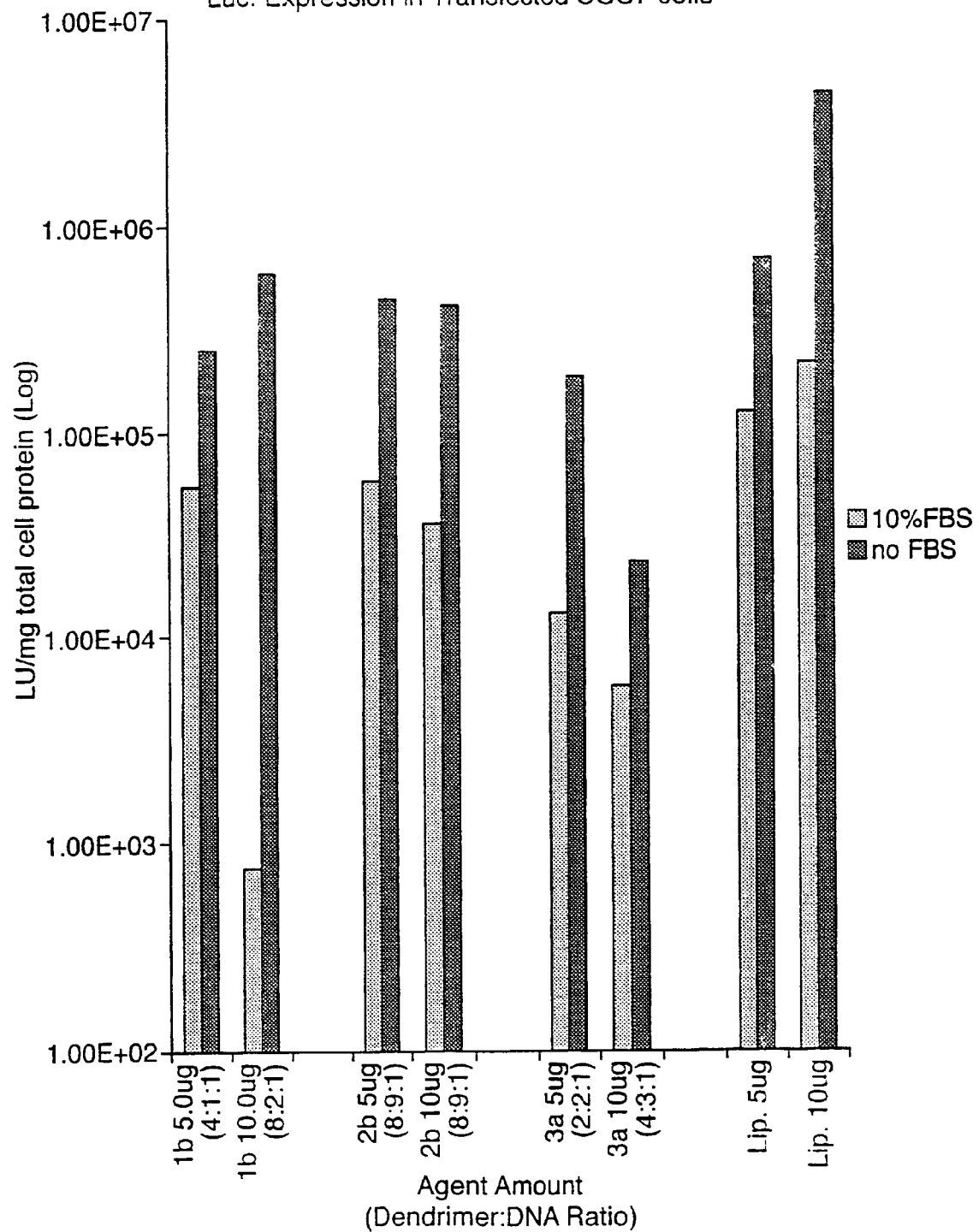

SEQUENCE LISTING

<160> NUMBER OF SEQ ID NOS: 6

<210> SEQ ID NO 1
<211> LENGTH: 24
<212> TYPE: DNA
<213> ORGANISM: Homo sapiens

<400> SEQUENCE: 1
caggtagtat cttctggtgg cact 24

<210> SEQ ID NO 2
<211> LENGTH: 7
<212> TYPE: PRT
<213> ORGANISM: Simian virus 40

<400> SEQUENCE: 2

Pro Lys Lys Lys Arg Lys Val
 1               5

<210> SEQ ID NO 3
<211> LENGTH: 9
<212> TYPE: PRT
<213> ORGANISM: Simian virus 40

<400> SEQUENCE: 3

```
Gly Pro Lys Lys Lys Arg Lys Val Gly
  1               5
```

```
<210> SEQ ID NO 4
<211> LENGTH: 18
<212> TYPE: DNA
<213> ORGANISM: Homo sapiens

<400> SEQUENCE: 4
agtgccacca gaagatac                                              18

<210> SEQ ID NO 5
<211> LENGTH: 24
<212> TYPE: DNA
<213> ORGANISM: Homo sapiens

<400> SEQUENCE: 5
cagggcctct cactaactaa tcac                                       24

<210> SEQ ID NO 6
<211> LENGTH: 24
<212> TYPE: DNA
<213> ORGANISM: Homo sapiens

<400> SEQUENCE: 6
cagccggatc ataatcagcc atac                                       24
```

CATIONIC COMPOUNDS AND THEIR USE AS MACRO MOLECULAR CARRIERS

The present invention relates to dendrimers having lipophilic pendant groups and cationic surface groups and their use as carriers for various counterionically charged peptides and protein therapeutic agents and oligo- and poly-nucleotides.

Linear poly(D-lysine) molecules, one of the most impressive macromolecular carriers, have been extensively studied and used to deliver proteins and therapeutic agents in vitro and in vivo. They have been shown to increase both the rate and the extent of adsorption through an endocytosis mechanism. The carrier properties of polylysines are known to be mediated via interactions between the cationic lysyl residues of polylysines and the negatively charged residues present on the surfaces of most cells and biological barriers. However, the linear polylysines are relatively cytotoxic and by themselves not very efficient, which limits their usefulness as drug carriers and agents to aid nucleic acid transfection of cells in culture.

Zhou, X., et al in Biochem. Biophys. Acta, 1065 (1991), 8–14 describe conjugation of low molecular weight poly(L-lysine)(PLL) to a phospholipid, through the amine group of the ethanolamine polar head group via a glutaric acid moiety conjugated thereto by a peptide bond. The amphiphilic compound is used as a carrier to promote DNA-mediated transfection in cultured mammalian cells. The conjugate is made by reacting two equivalents of phospholipid for each mole of polylysine and it is estimated that the product has two phospholipids per 16 lysine residues on average. The process used to make the compound inevitably results in a mixture of products. However the conjugated polylysines did have improved transfection activity as compared to polylysine itself.

Bielinska, A., et al in Nucleic Acids Res.(1996), 24 (11) 2176–2182 describe dendritic (or Starburst™) polyamidoamine dendrimers, said to have a spherical shape with high density cationic surface charge. The polymers are used in place of cationic liposomes (such as Lipofectin) to deliver plasmids and antisense oligonucleotides into cell lines. Delivery of antisense cDNA or antisense oligonucleotides into cell lines permanently expressing luciferase genes resulted in dose dependent inhibition of luciferase expression. The dendrimers were said not to be cytotoxic at the concentrations effective for DNA transfer. These polymers have been described by Haensler J and Szoka F. C. Jr, Bioconjugate Chem. 4, 372–379 (1993) to mediate transfection of cells in culture. In WO-A-98/40502 cationic liposomes and oligo-cationically modified oligo peptides are used in combination to enhance transfection efficiency of DNA. The oligo peptides are linear and do not have hydrophobic anchor moieties.

Kabanov, A V. and Kabanov, V A. in Bioconjugate Chem. (1995) 6, 7–20, describe the use of various hydrophobised polycations to deliver foreign nucleic acids into contact cells. Linear polylysines are conjugated to the amine group of phosphatidylethanolamines as in Zhou et al (op. cit.). Lipospermine compounds have N,N-dialkylated spermine derivatives. These and other hydrophobised polycations are said to become incorporated into liposomes through the long chain alkyl substituent serving as anchors for the compound in the liposome membrane.

Vinogradov, S V. et al in Bioconjugate Chem.(1996), 7, 3–6, describe block polycationic-oligo nucleotide polymers. The blocks were synthesised using nucleotide synthetic techniques, firstly to generate the polycationic block (formed from the monomer H-phosphonate of 1-O(4,4'-dimethoxytrityl)-1,3-butanediol followed by introduction of amino groups using 1,4-diaminobutane. The oligonucleotide was an antisense polynucleotide complimentary to the splicing site of immediately early mRNA 4 and 5 of herpes simplex virus type 1(HSV-1). The block copolymer inhibited the reproduction of HSV-1 and the effect was increased by conjugating cholesterol to the end of the oligo nucleotide opposite to that which the polycationic block was conjugated.

In Pharm.Res. 15 776–782 (1998) Sakthivel T. et al describe the synthesis of a range of peptide dendrimers having lipophilic surfaces. The surface pressure-area characteristics are determined at the air-water interface, giving values of the limiting surface areas from 0.4 $nm^2$ to 8.8 $nm^2$, in good agreement with the areas anticipated from computer generated molecular models (0.5 $nm^2$ to 6.5 $nm^2$). Surface pressure isotherms indicated the expected scaling relationships between the area per molecule and the molecular weights of these compounds. Dendrimer compounds having such surface hydrophobic groups, as well as other surface groups such as amino groups of lysine residues, are described in our earlier application number EP-A-0884327. They are used to form conjugates for instance by covalent reaction of the amine groups with ligands such as antigens, drugs, targeting moieties or hydrophilic groups.

Dendrimers having core lipidic amino acid moieties are described in our earlier publication WO-A-94/02506. These dendrimers had surface amino groups conjugated to active moieties such as peptide antigens, and were used to deliver such active compounds in vivo.

In the invention there is provided a new complex comprising, in admixture, a cationic polymer compound and an anionic active compound, characterised in that the polymer compound comprises a dendritic core having at least one dendron having n levels of dendritically linked trifunctional monomer units, cationic groups at at least 50% of the terminal branches of the at least one dendron, and an anchor moiety comprising at least two lipophilic $C_{6-24}$-alkyl, -alkenyl or -alkynyl groups covalently conjugated in the polymer compound.

The invention comprises also the new use of a cationic polymer compound comprising a dendritic core having at least one dendron having n levels of dendritically linked trifunctional monomer units, cationic groups at at least 50% of the terminal branches of the at least one dendron and an anchor moiety comprising at least two $C_{6-24}$alkyl, -alkenyl or -alkynyl groups covalently bound into the polymer compound, in the manufacture of a composition for use in a method of treating a human or animal in which method an anionic therapeutically active agent is administered in the form of a complex with the cationic polymer compound.

In the present specification a "dendritic core" comprises a focal unit to which is joined at least two, usually two, branches. Each branch may in turn effectively form a focal unit and two or more branches. The first level of the said at least one dendron or a trifunctional group to which that dendron and a further dendron is attached act as a focal group which may form a link to other components of the cationic polymer.

The complex is generally provided in the form of a composition comprising also a carrier. The composition of the invention may be a pharmaceutical composition, in which case it comprises a pharmaceutically acceptable carrier.

In the context of the present invention, a trifunctional monomer contains three functional moieties which react with functional moieties on other monomer units to form a polymer chain. Although these functional groups on any one monomer type may all be of the same type or all be different, it is preferred that functional groups be one of two different types, the different types being coreactive with one another but not homoreactive. A preferred monomer therefore contains two functional groups of one type and one functional group of the other type. Preferred functional groups are carboxylic acid groups and amine groups. Alternatively the dendritic molecule may be any of those described in the review by Tomalia, D. A. et al in Angew. Chem. Int. Ed. Engl. 29 138–175 (1990), the disclosure of which is incorporated herein by reference.

Tomalia et al describe topologies of dendrimers, indicating that the terminal branches are generally found at the surfaces of the three dimensional structures. By providing cationic groups at the terminal branches of at least one dendron, the polymer compound is believed to have cationic charges at its surface. Preferably cationic groups are .$NR^5_3$ groups in which the $R^5$ groups are the same or different and are hydrogen or $C_{1-4}$alkyl, preferably hydrogen.

In the invention the dendritic core of the polymer compound is preferably formed of dendritically linked amino acid monomer units each being of the formula I

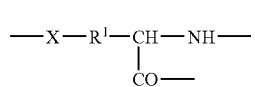

I in which $R^1$ is $C_{1-6}$-alkanediyl, and X is —O—, —S—, —NH—, or —CO—. Where, in the dendritic units, X is NH, the cationic terminal groups may be derived from the —X—groups of the terminal monomer units. Where the dendritic linkage of such terminal units is through the —CO—group of the unit, both the group —X—and the amine group of the unit of the formula I may generate cationic groups, for instance of the formula —.$NH_2R^5$ in which $R^5$ is hydrogen or a lower alkyl group.

Alternatively, the cationic groups may be reacted onto the dendron terminal branches at an appropriate stage of the synthesis.

Preferred groups $R^1$ are linear $C_{2-4}$-alkanediyl, more preferably $C_{3\ or\ 4}$-alkanediyl The anchor moiety may be provided to one of the terminal groups of the said at least one dendron, or to a focal unit as a group joined to the focal or core unit of the polymer (dendrimer). Alternatively the dendrimer may comprise a second dendron emanating from a focal unit to which the 1st level of the said at least one dendron is attached, to the terminal groups of which lipophilic groups are attached. In this, less preferred, embodiment the anchor moiety may be located at the surface of the three dimensional dendrimer structure, where the second dendron is appropriately configured preferably the anchor moiety is joined to the core.

Where the dendrimer is formed of dendritically linked amino acid units, these are conveniently synthesised using solid state peptide synthetic techniques. It is convenient for the anchor moiety to be synthesised using these same techniques. It is convenient for the anchor to be formed from lipidic amino acid units joined together by peptide groups in a linear oligopeptide anchor component. It is believed that anchoring properties are optimised when the two or more lipophilic groups are close to one another in the molecule. Preferably they are joined, optionally through linker groups, to adjacent units forming a linear oligo peptide polymer backbone. In the preferred embodiment where the anchor is joined to a focal unit of a dendrimer, lipidic amino acids are joined through peptide bonds to one another and to the focal unit of the dendrimer. Such oligopeptide lipidic amino acid anchor components have the formula II

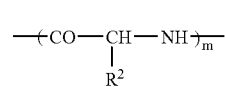

II in which $R^2$ is a $C_{6-24}$-alkyl, -alkenyl or -alkynyl group and m is at least 2.

Where the anchor moiety comprises lipophilic groups joined to the terminal groups of a second dendron, and the lipophilic groups are joined by peptide bonds to one or more terminal groups of that dendron, an oligopeptide of the formula II may be joined to one terminal group or each of the at least two lipophilic groups may be joined to one thermal group. In the latter case the lipophilic groups each have the formula III

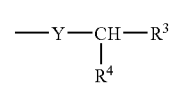

III in which Y is —CO—, —NH—, —O— or —S—;

$R^3$ is an organic group containing at least one $C_{6-24}$-alkyl, -alkenyl or -alkynyl group; and $R^4$ is hydrogen, amine, protected amine, blocked amine, hydroxyl, blocked hydroxyl, thiol, blocked thiol, carboxylic or blocked carboxylic a $C_{1-5}$-alkyl, -alkenyl or -alkynyl group or is a group selected from the same groups as $R^3$.

Preferably $R^3$ is a $C_{6-24}$-alkyl, -alkenyl or -alkynyl group

Preferably Y is —CO—. Preferably $R^4$ is a blocked amino group, most preferably an acylamino group, such as acetylamino.

Where the polymer comprises a first dendron of dendritically linked amino acid units, with lipophilic groups conjugated to terminal branches, the cationic polypeptide moiety preferably comprises a second dendron joined to a common focal group with the first dendron. The second dendron preferably comprises n levels of dendritically linked amino acid groups of the formula I, at the $2^{n'}$ terminal branches of which there are cationic groups. The value of n of the second dendron is preferably 2.

The value of n of the at least one first dendron is preferably in the range 2 to 6, more preferably 3–5, most preferably 4 or 5.

According to a further aspect of the present invention, there is provided a new complex comprising in admixture a cationic hydrophobised polypeptide compound and an anionic active compound, characterised in that the polypeptide compound comprises a cationic polypeptide moiety formed from amino acid units having pendant amine groups, and an anchor moiety joined to the cationic polypeptide moiety through peptide bonds, the anchor moiety comprising at least two groups of the formula IV

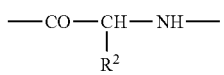

IV in which $R^2$ is a $C_{6-24}$-alkyl, -alkenyl or a -alkynyl group.

The units of the formula IV may be joined directly to one another by peptide bonds to form a linear oligopeptide component, for instance which is attached to the cationic polypeptide moiety by peptide bonds. Alternatively each of the groups of the formula IV may be joined to separate pendant groups (which may be the amine groups or may be other functional groups) of the cationic polypeptide moiety either through the NH linkage or, preferably, through the CO linkage of the formula IV. The other of the groups CO and NH may be blocked using a suitable carboxylic or amine blocking group, respectively.

The cationic polypeptide moiety may be linear polyL-lysine or polyD-lysine. An anchor which is formed of a linear oligo peptide formed from lipidic amino acid units of the formula II, may be joined directly to the linear polylysine at either or both ends of the chain or to one or more of the w-amine groups of lysine units mid way along the chain. Alternatively blocks or individual lipidic amino acid units of the formula IV may be part of the main polylysine chain.

The dendrimers described above may comprise other ligands covalently attached as pendant groups, to terminal groups of branches or to the focal group or group attached to the focal group, such as to the oligopeptide anchor. Such ligands may be for instance targeting moieties, especially nuclear localisation oligopeptides, or sugar molecules.

In the aspects of the invention described above, the active compound is generally used in therapy. The invention is of particular benefit in the delivery of nucleic acids into cells. The anionic active compound is thus preferably a nucleic acid, for instance RNA or, preferably, DNA. The DNA may be single stranded or double stranded and may be linear or circular. The invention is shown below to provide improved transfection for oligonucleotides and plasmid DNA. The invention may be used for in vivo use for delivering the active compound to a human or an animal, for instance in need of gene delivery. It is of particular value in the delivery of genes encoding clotting factors, especially factor IX. The dendrimer/nucleic acid complex may be delivered direct into the circulation, intramuscularly, intraperitoneally, to the mucosa, to the lungs or orally. The invention is also of use in in vitro analyses for delivering active compounds especially nucleic acids to cells in culture. Such in vitro analytical methods form a further aspect of the invention. The invention is also of use to make therapeutic agents by culturing transfected cells expressing the gene.

According to a further aspect of the invention there is provided a complex formed of an oligo- or poly-nucleotide and an anchored cationic polypeptide compound, in which the polypeptide compound comprises a core having at least one dendron of n levels of dendritically linked amino acid units of the formula I, and having cationic groups at at least 50% of the terminal branches and comprising an anchoring moiety conjugated to the polypeptide core, preferably through peptide bonds. n is preferably 3, 4 or 5, more preferably 3, or most preferably 4.

In this aspect of the invention the oligo or polynucleotide may be counterionically bound to the cationic polypeptide or may alternatively be covalently conjugated to it. Preferably the oligo- or poly-nucleotide is counterionically bound. The ratio of charges of the cationic polypeptide to nucleotide is generally more than 1, for instance in the range 1:(0.8–0.05), preferably 1: (0.8–0.2), more preferably in the range 1:(0.7–0.3). These ratios also apply to the ratio of cationic equivalents to anionic equivalents in the first two aspect of the invention.

In this third aspect of the invention, the anchor moiety is preferably joined by peptide bonds to the cationic polypeptide core but may, alternatively, be joined by ester linkages such as are described by Tam et al in Proc.Nat.Acad. Sci.USA 85, 5409–5413 (1988) or by the phosphatidyl linkers described by Zhou et al and Kabanov et al, op. cit.

According to a fourth aspect of the present invention there is provided a new composition comprising, in admixture an anchored cationic polypeptide compound, comprising a cationic polypeptide moiety and an anchor moiety comprising at least two units of the formula IV, and an oligo- or poly-nucleotides for delivery of the nucleotide into cells.

In all aspects of the invention the counterionic complex is preferably formed and used in an environment in which substantially all of the cationic groups are ionised. Where the cationic groups—$NR^5_3$ have all three $R^5$ groups as hydrogen, the pH of the medium is preferably less than about 10, more preferably in the range 5–9.

The invention is illustrated in the accompanying examples. The figures herein relate to the examples as follows:

FIGS. 1 to 3 are the formulae for specifically exemplified compounds synthesised in Example 1;

Figure 5A:
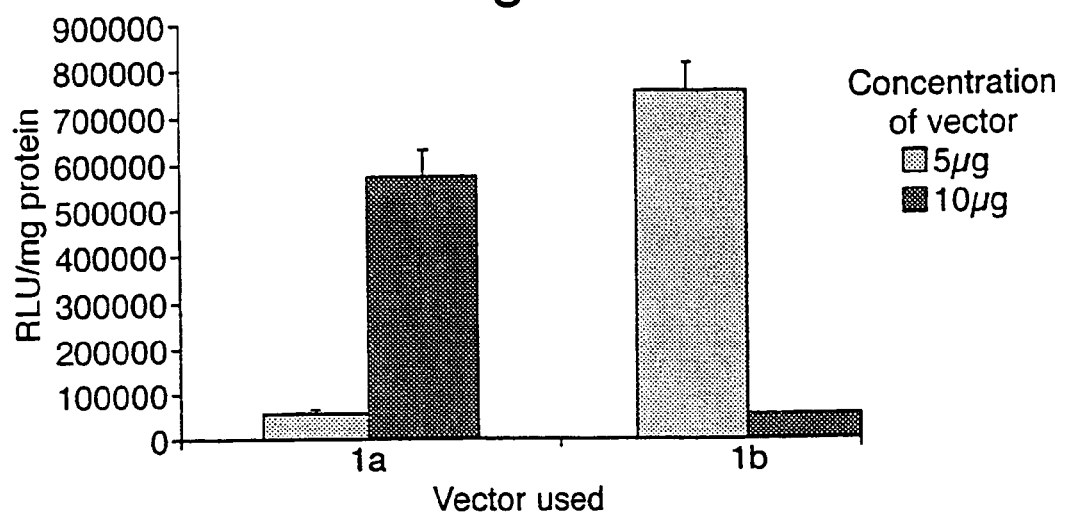
Figure 7:
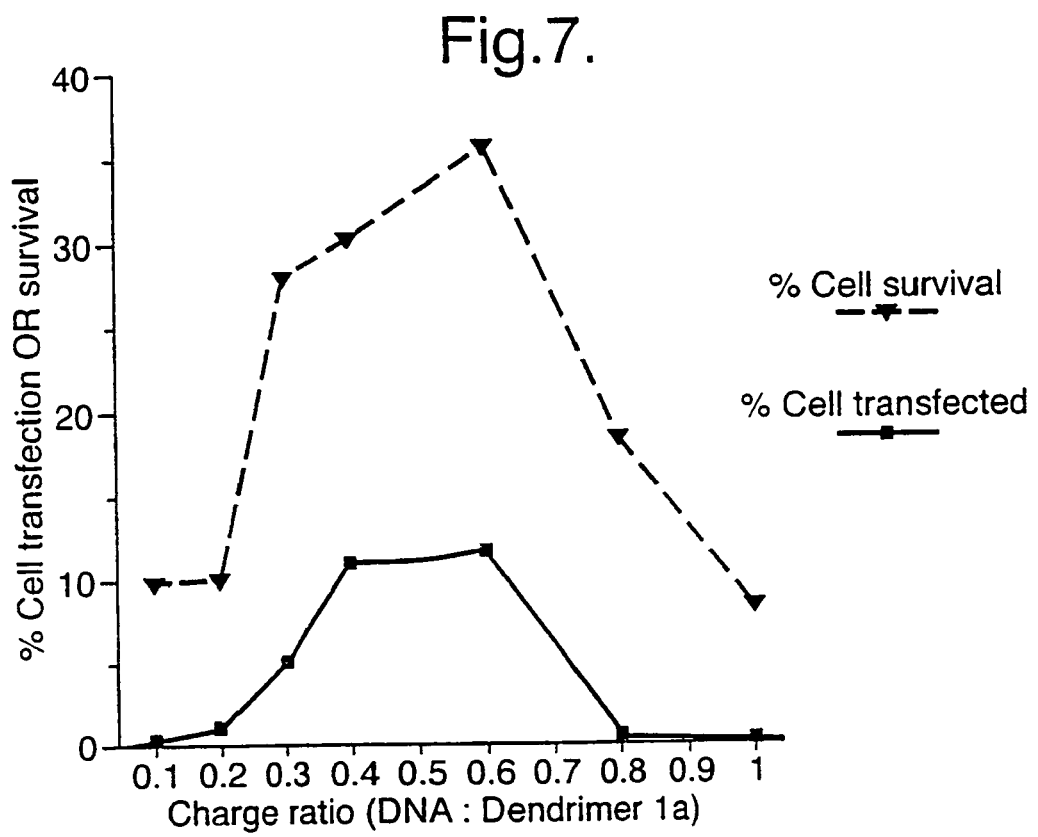
Figure 8:
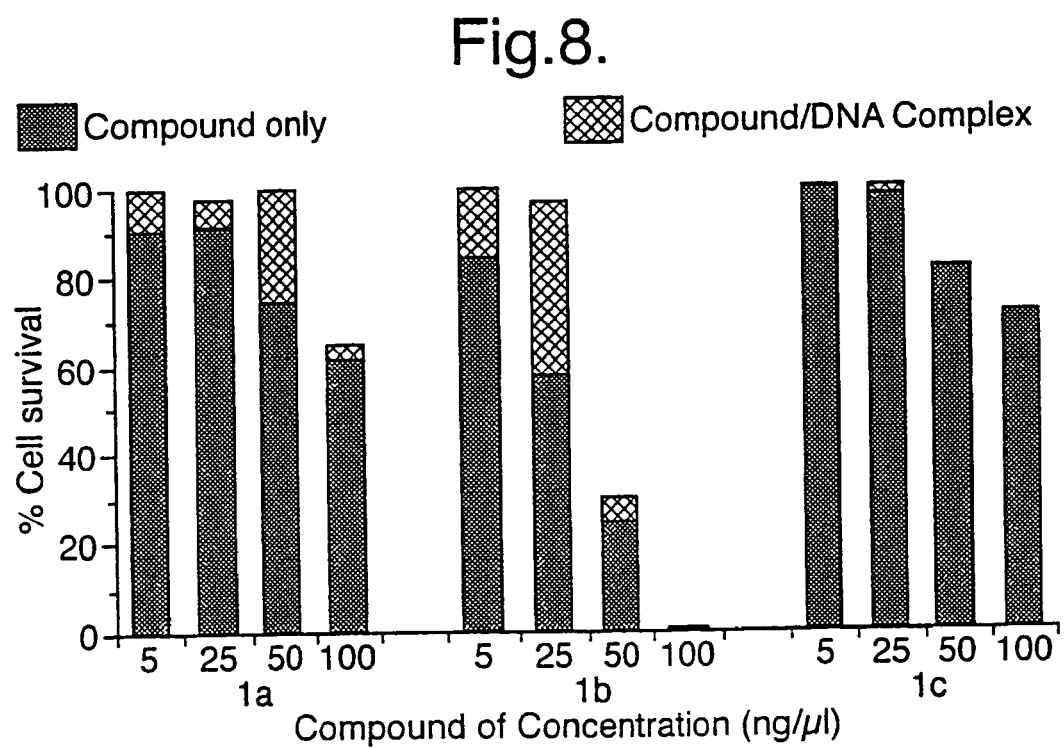

FIGS. 5a and b show the results of Example 3;

FIG. 6 shows the results of Example 6;

FIG. 7 shows the results of Example 8;

FIG. 8 shows the results of Example 9; and

Figure 9:
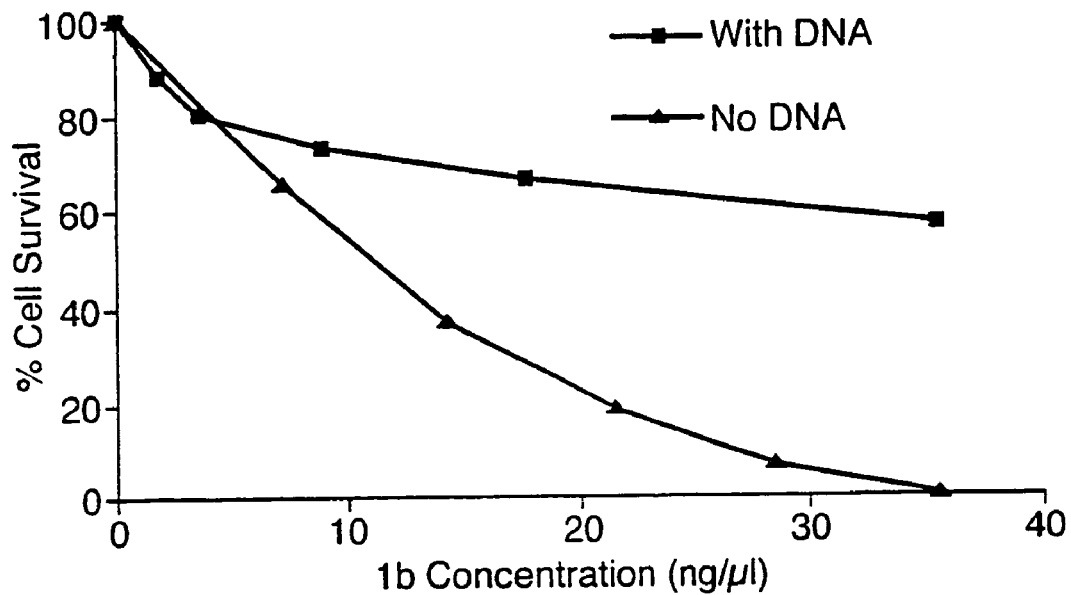
Figure 10:
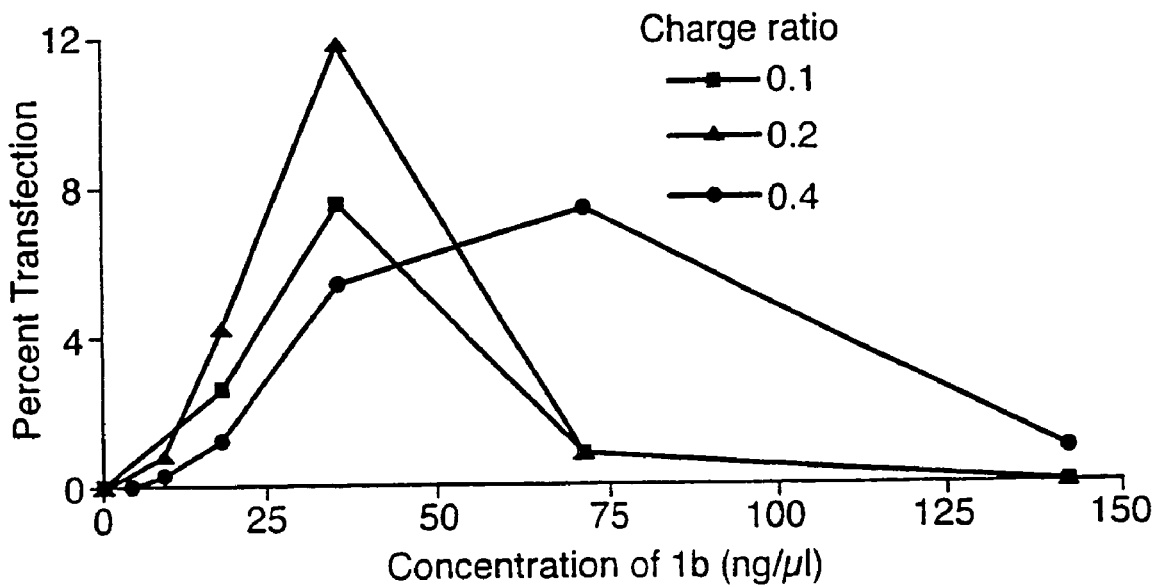

FIGS. 9 and 10 show the results of Example 10.

FIG. 11 shows some of the results of Example 3.

Materials

4-Methyl benzhydrylamine (MBHA) resin, protected [tert-butyloxycarbonyl (Boc) and fluorenylmethoxycarbonyl (Fmoc)] amino acids were obtained from Novabiochem, UK, 2-(1H benzotriazol-1-yl)-1,3,3-tetramethyluronium hexafluoro phosphate (HBTU) from Phase Separations Ltd, UK, trifluoroacetic acid (TFA) from Halocarbon Products Corporation, USA, hydrogen fluoride gas (HF) from BOC, UK, diisopropyl ethyl amine (DIEA) from Fluka, Switzerland and dimethylformamide (DMF) from Rathburn, UK. Boc-Orn-(Boc)-OH and N-α-(tetra-O-acetyl-β-D-glucopyranosyl)-$N^α$-tert-butoxycarbonyl benzyl asparagine were synthesised and purified by the inventors. pGL3 Basic and pGL3 Control vectors and luciferase assay reagents were purchased from Promega. The former has no promoter to drive the luciferase gene expression whereas in the latter, luciferase expression is driven by the SV40 promoter. Plasmid DNA was purified from maxi cultures in LB broth using Qiagen kit as instructed. Synthesis and purification of the protected lipidic amino acid

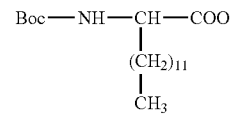

is as described in Gibbons, W. A. et al Liebigs Ann.Chem. 1990, 1177–1183.

X-Gal is an indoxyl derivative which is a chromogenic substrate for beta galactosidase. It is commercially available and is used according to the supplier's instructions.

pSVβ gal plasmid is obtained from Promega and is cultured to provide large scale batches for use in the experiments by DH5α E. coli by standard methods including final CsCl density centrifugation step.

MTT test used according to Freshney, R. I. in "Culture of animal cells".

EXAMPLE 1

Synthesis of Dendrimers Having Anchor Groups

Solid phase peptide synthetic methods were used employing 1 g of a polyacrylamide resin having a degree of substitution of 0.46 mmol/g resin. The reaction to form dendrimers with surface lipophilic groups (compounds 4a–c is described in more detail by Saktivel, T. et al Pharm.Res. 15, 776–782 (1998). The method of forming the dendrimers with lipophilic groups attached at the core is described in earlier application WO-A-9402506. The step involving deprotection of Boc was performed in 100% trifluoroacetic acid. Couplings of pendant amine groups on the bound compound with carboxylic acid groups of amino acid reagents having protected amine groups was achieved using a three fold excess of HBTU activated Boc-amino acids in dimethylformamide in the presence of diisopropylethyl amine. Acidulation of deprotected Boc group of lipoamino acid was carried out in the presence of diisopropylethyl amine. Deprotection of the Fmoc group to form the second dendron was carried out with 20% bipyridine in DMF. Deacetylation of sugar-containing dendrimers was performed using hydrazine in methanol. The protection of the N-termini was performed in 100% TFA in all couplings the efficiency was greater than 99% as indicated by quantitative ninhydrin tests.

The resin peptide was carefully flow washed before and after each deprotection step. The final product was washed with dichloromethane and dried in air. The peptide was removed from the resin support with a high HF method 2 g resin peptide, 20 ml HF, 1.5 hour at −5° C., p-cresol 2 g, scavenger) to yield the crude peptide which was washed with ether to remove the p-cresol and dissolved in 95% acetic acid and lyophilised.

Purification

Analytical HPLC separation of the synthesised dendrimers was carried out on a 25 cm Vydac $C_{18}$ RAC column with 5 μm pore size and 4.6 mm internal diameter. Following standard degassing techniques, particulate matter was removed from HPLC grade acetonitrile and water using membrane filters. Analytical separation was achieved with a solvent gradient beginning with 0% acetonitrile, increasing to 60% acetonitrile at 20 min. maintaining at this concentration for 20 min and decreasing steadily to 0% acetonitrile for 10 min at a constant flow of 1.2 ml min$^{-1}$.

For preparative separation a TSK-GEL preparative $C_{18}$ column with 10 μm pore size and 2.5 cm internal diameter was used. Separation was achieved with a solvent gradient beginning with 0% acetonitrile, increasing constantly to 18% acetonitrile at 60 min then 60% acetonitrile at 80 min, staying at this concentration for further 30 min and decreasing steadily to 0% acetonitrile for 30 min at a constant flow of 8 ml min$^{-1}$. The gradient was effected by two microprocessor-controlled Gilson 302 single piston pumps. Compounds were detected with a Waters 486 tunable absorbance detector at 214 nm or a Holocrome UV-VIS detector 220 nm. Mass spectra were run on VG Analytical Tofspec instrument, using matrix assisted laser desorption (MALD) ionisation at a wavelength of 337 nm generated by a nitrogen laser.

Compounds synthesised using the general technique mentioned above are shown in FIGS. 1 to 3 and analytical results are in Table 1.

EXAMPLE 2

Interaction of Conjugates with DNA 2.1 Electron Microscopy

Various amounts of the compounds 1a and 1b were mixed with 2.5 μg plasmid DNA (pGL3) diluted in sterile distilled water to give a total volume of 100 μl. After incubation at room temperature for 30 mins, DNA-dendrimer complexes were spotted on G300HS copper grids (Gilder, Grantham, UK) precoated with Pioloform (TAAB Laboratories, Aldermaston, UK). After drying, the samples were stained with 1% phosphotungstic pH 6.7 (BDH) and viewed under a Zeiss electron microscope.

The results show the formation of approximately spherical or toroidal structures in the presence of the dendrimers as compared to extended forms visible in the absence of dendrimer.

2.2 Mobility Shift Assays

Dendrimers (1a–c and 2a–c) and pGL3 plasmid DNA (2.5 μg) were separately diluted in sterile water, and the solutions mixed in a 1:1 (vol) ratio. To investigate the effect charge ratios of DNA to dendrimer, various concentrations of dendrimer were used. After complex formation, samples were resolved on 0.8% agarose gel. Uncomplexed, naked plasmid DNA was used as control for shifts. Ethidium bromide was used to develop the gel.

To determine the interaction of dendrimers with oligonucleotides, 100 pmols of a 24nt sequence complementary to the 5' terminus of human Factor VII cDNA [CAGGTAG-TATCTTCTGGTGGCACT](Seq. ID No. 1), was end-labelled with γ-32P[ATP] and T4 polynucleotide kinase according to standard techniques. Aliquots of the labelled oligonucleotide were incubated with various concentrations of dendrimers 1a and 1b diluted in sterile water. After incubation for 30 mins at room temperature, the samples were resolved on a 5–10% non-denaturing polyacrylamide gel. The gel was directly exposed to X-ray film for 1 hr and developed.

For the plasmid DNA the lower amounts of dendrimer contribute to a mobility shift of the plasmid consistent with an increase in molecular weight due to complex formation between one plasmid and one or more dendrimer molecules and/or a reduction in anionic charge/weight ratio. For higher levels of dendrimer the plasmid/dendrimer does not move from the well. If the gel is left running for a longer period some reverse movement of material (non-nucleotide) can be detected, i.e. in the opposite direction to plasmid mobility. These results are consistent with the formation of large complexes between multiple plasmids and multiple dendrimers at around equivalent levels of positive and negative charges. When dendrimer is present in excess quantities there appears to be uncomplexed dendrimer which is mobile in the reverse direction. Furthermore the quantities of the dendrimers having different levels of amino groups to achieve non-mobile complex formation is about 10 μg (for 2.5 μg DNA) for compounds 1a and 2a, which have 8 amine groups per molecule, about 5 μg for compounds 1b and 2b which have 16 amine groups per molecule and about 2.5 μg for compounds 1c and 2c which have 32 amine groups per molecule. Thus an approximate doubling of the change ratio for the dendrimer leads to approximately a halving of the weight of dendrimer needed These results indicate the interaction of DNA and dendrimer is a one-to-one counterionic attraction.

The results using end labelled oligonucleotides show similar levels of dendrimer:DNA ratios for the mobility shifts.

2.3 Nuclease Protection Assay

Plasmid DNA (5 µg) and dendrimers 1a and 1b were separately diluted in sterile water. Equal volumes of dendrimers and DNA were then mixed (final volume, 100 µl) and incubated at room temperature for 30 mins. 45 µl of this was then incubated with 10 units/ml of DNase I (Boehringer Mannheim) and 0.5X universal buffer (Stratagene) to a final volume of 50 µl. Following incubation for 15 mins at 37° C., aliquots of the reaction mixtures were co-resolved on 0.8% agarose gel and developed with ethidium bromide. Supercoiled uncomplexed plasmid was used as a control for nuclease digestion.

The results are consistent with the mobility shift date and show that at similar relative levels to those for fully complexing DNA, complete protection from DNase I digestion is achieved.

2.4 Zeta Potential Measurements of Complexes

Figure 4:
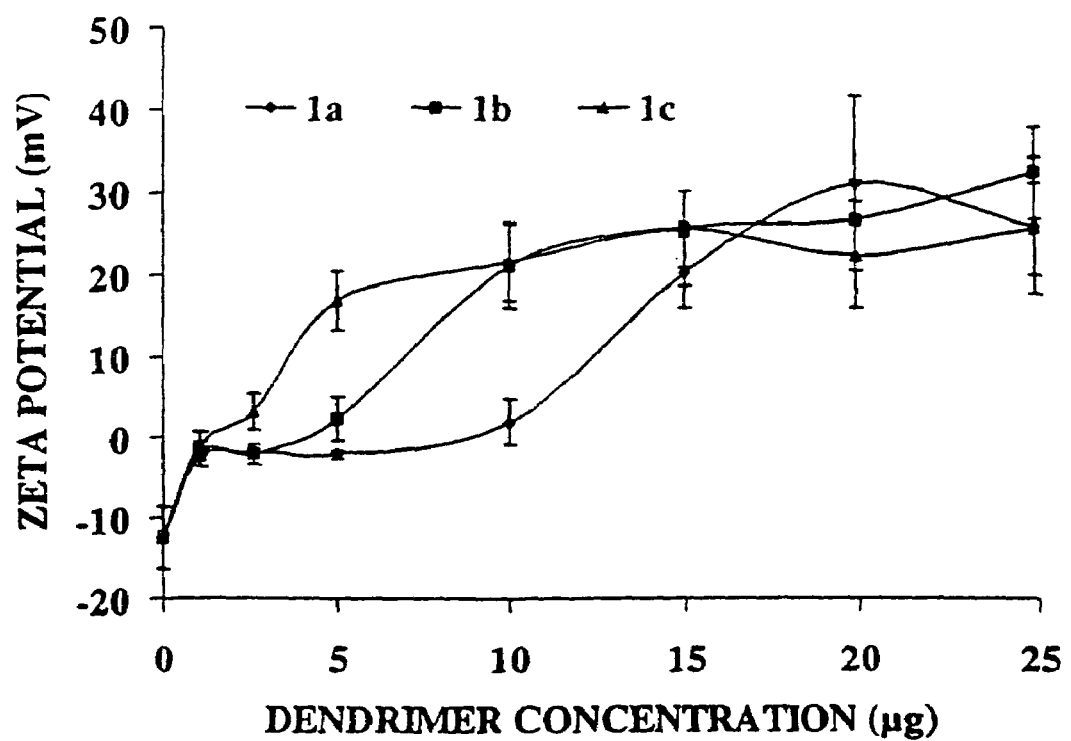
FIG. 4 shows the results of Example 2.4.

10 µl of the dendrimer (1a–c)/DNA (pGL3 plasmid) complex from Example 2.2 was diluted to 5 ml with 10 times diluted PBS. Samples were placed in the Zeta-sizer (Malvern Instruments, Malvern Pa.) and analysed immediately. Five repeat measurements were taken, with 30 s intervals in between measurements to equilibrate the samples. Although adsorption of the cationic dendrimers onto the negatively charged cuvette was noticeable, this appeared not to interfere with the reproducibility of the measurements. The results are shown in FIG. 4. The zeta potential is believed to affect transfection efficiency as it does for cationic liposomes used as gene delivery vectors.

Conclusions

Based on the results obtained from the DNA/complex formation, zeta potential measurements and DNase I protection, the concentration of dendrimers to be used for the transfection experiments (Examples 3–6) was fixed at 10 µg/ml for the dendrimers with 8 free amino terminals and 5 µg/ml and 2.5 µg/ml for the dendrimers with 16 and 32 free amino terminals respectively.

EXAMPLE 3

Cell Culture and Transfection

The SV40- transformed renal epithelial cell line derived from African Green Monkey (ECACC. Accession No. 87021302 Salisbury) COS-7 cells were cultured in Dulbecco's modified Eagle's medium DMEM/Glutamax I/4.5 g per 1 glucose (Life Technologies) and supplemented with 10% foetal calf serum and antibiotic/antimycotic mixture (Sigma). Cells were seeded in 6 cm dishes in 5 ml of medium and grown in 5% $CO_2$. 1–3 hrs before transfection, culture medium was replaced with 3 ml fresh medium. Luciferase reporter vector pGL3 Control and pGL3 Basic vectors (Promega) were prepared on Qiagen column. 2.5 µg of each plasmid was diluted separately in OptiMEM I (Life technologies). Dendrimers were similarly diluted and incubated with equal volumes of the diluted plasmid DNA (total volume 100 µl) for 30 mins at room temperature. The DNA-dendrimer complexes were added to the cells. After 6–12 hrs, 2 ml of fresh medium was added to the culture, and incubation continued for a further 48 hrs. Luciferase activity was determined with an assay reagent as suggested, and measured in an LKB Wallac luminometer. Protein content in 10 µl lysates was determined in microtitre plates (Nunc) with the Dc (detergent compatible) Protein Assay system (BioRad) to normalise luciferase activity to cell mass.

Figure 5B:
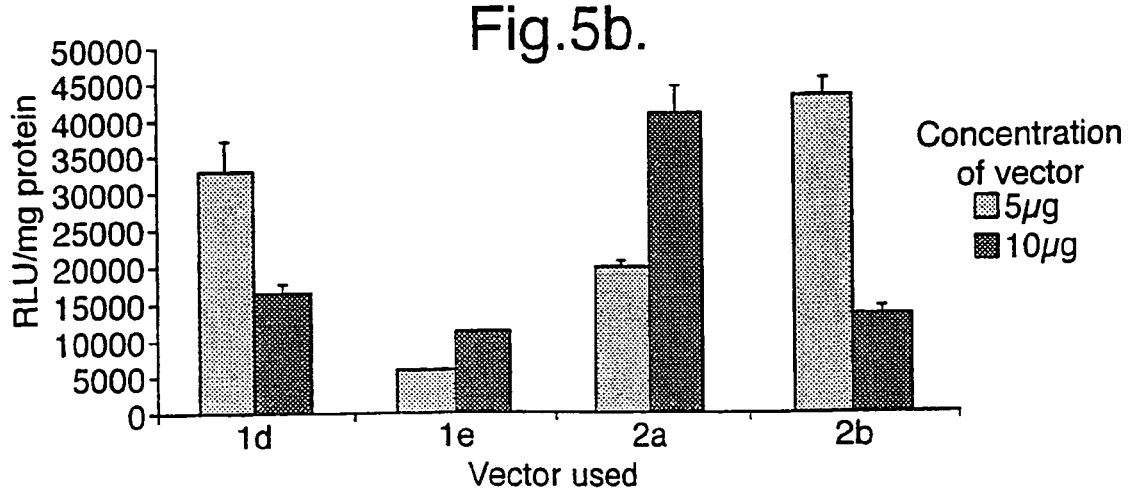

Results are shown in Table 1 and FIG. 5 which show the transfection and expression of luciferase reporter in COS-7 cells with dendrimers. FIG. 5A: Unmodified dendrimers 1a and 1b at two concentrations; FIG. 5B 1d and 1e are respective modifications of the above, with the SV40 nuclear localisation signal sequence. 2a and 2b are ornithine derivatives of the same respective templates 1a and 1b. Values are averages of at least three replications.

The results show that optimum transfection efficiency is achieved at approximately the same dendrimer:DNA ratios as for mobility shift and Dnase I protection.

Since nuclear delivery is the rate-limiting step in gene transfer, we incorporated a nuclear localisation signal [PKKKRKV](Seq. ID No. 2) derived from the large T antigen of SV40. However, this reduced transfection efficiency in a manner that is not presently understood. Steric hindrance may be one possible explanation. The function of this sequence may also be context-dependent. Since COS-7 cells constitutively produce this protein, it is possible that high concentrations of this peptide might be repressive. However, the position of this motif will be altered to monitor transfection efficiency. While there was negligible reporter activity with the pGL3 basic (promoterless) vector, transfection efficiency was not serum dependent, as comparable levels of uptake were observed with and without serum (data not shown). Maximum levels of transfection were observed with compounds 1a ($5.7 \times 10^5$ RLU/mg protein) and 1b ($7.5 \times 10^5$ RLU/mg protein). Of the dendrimers reported to enhance delivery of genes and oligonucleotides in the prior art by Haensler J. and Szoka, F. C.Jr.op.cit., the greatest increase in gene transfection has been seen with generation 4 and 5 polyamidoamine dendrimers. This difference between generations was not evident in our transport of pGL3 basic, which demonstrated similar transport enhancement for all generations tested. The differences could be due to the differences in cell lines tested or changes in the final size of the complex.

When in the dendrimers the amino group provided by lysines were replaced by ornithine in which the amino functions were separated by 4 (rather than 5)carbon long alkyl chains, transfection experiments could not be performed due to the poor solubility of the resulting compounds 2a and 2b. The more soluble ornithine containing dendrimer 2c ($1.5 \times 10^5$ RLU/mg protein) exhibited higher level of transfection than its analogue with lysine building block (compound 1c; $6.0 \times 10^4$ RLU/mg protein).

For targeting purposes, compounds 3a–c with a carbohydrate moiety were used. When a sugar molecule was introduced to the dendrimer, the transfection activity of the compounds was not improved but the activity of the compounds was preserved.

We have synthesised complex dendrimers containing large lipidic and charged complex dendritic moieties in the same construct. This kind of change of the lipid attachment reduced the transfection activity of the compounds 4a–c considerably.

To target the delivered gene within the cell into the nucleus and to improve the transfection activity of the complexes, we have attached a nuclear localisation peptide (NLS) to the dendrimer resulted in compounds 1d, 1e, 2d and 2e. Unfortunately, the presence of NLS peptide in the dendrimer did not improve the transfection. Roberts et al Cell 50, 465 (1987) inserted the SV 40 large T antigen signal into different parts of chicken pyruvate kinase; nuclear transport was not observed when the targeting sequence was inserted into a part of the pyruvate kinase molecule that was not exposed on the surface, suggesting that exposure of the NLS is required for it to function. The decreased activity of the NLS attached dendrimers could be due to the lack of exposure of the NLS on the surface.

Similar results are seen when BHK cells are used in place of COS-7.

Results of further experiments carried out in substantially the same way but, for half the tests, foetal calf serum (or foetal bovine serum, FBS) was omitted from the culture medium. For this series, a comparison with a known gene vector, lipofectamine at 5 µg and 10 µg, was also conducted. The results are shown in FIG. 11.

TABLE 1

| Compound | No. of amino groups | X | R | RLU/mg protein |
|---|---|---|---|---|
| 1a | 8 | H | — | $5.7 \times 10^5$(a) |
| 1b | 16 | H | LYS | $7.5 \times 10^5$(b) |
| 1c | 32 | H | LYS—[LYS]$_2$ | $6.0 \times 10^4$(c) |
| 1d | 8 | GPKKKRKVG (Seq. ID No. 3) | LYS | $1.7 \times 10^4$(a) |
| 1e | 16 | GPKKKRKVG (Seq. ID No. 3) | LYS—[LYS]$_2$ | $0.6 \times 10^4$(b) |
| 2a | 8 | H | — | — |
| 2b | 16 | H | ORN | — |
| 2c | 32 | H | ORN—[ORN]$_2$ | $1.5 \times 10^5$(c) |
| 2d | 8 | GPKKKRKVG (Seq. ID No. 3) | ORN | $4.0 \times 10^4$(a) |
| 2e | 16 | GPKKKRKVG (Seq. ID No. 3) | ORN—[ORN]$_2$ | $4.2 \times 10^4$(b) |
| 3a | 8 | Asp Glu | — | $1.1 \times 10^5$(a) |
| 3b | 16 | Asp Glu | LYS | $4.4 \times 10^4$(b) |
| 3c | 32 | Asp Glu | LYS—[LYS]$_2$ | $2.2 \times 10^4$(c) |
| 4a | 8 | Asp Glu | — | $1.0 \times 10^3$(a) |
| 4b | 16 | Asp Glu | LYS$_2$ | $8.6 \times 10^3$(b) |
| 4c | 32 | Asp Glu | LYS—[LYS]$_2$ | $1.0 \times 10^4$(c) |

Figure 2:
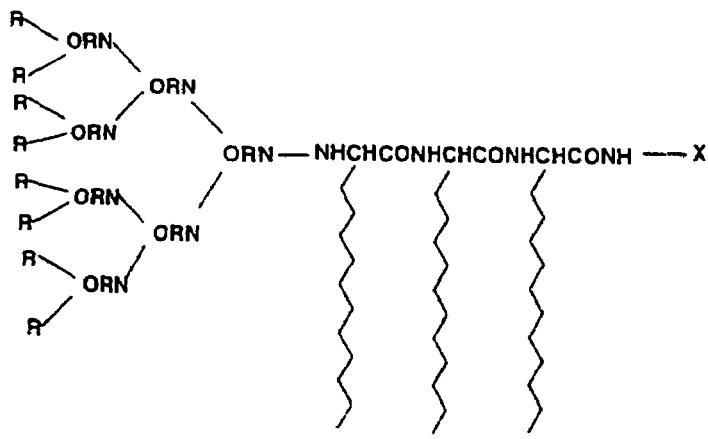
Figure 3:
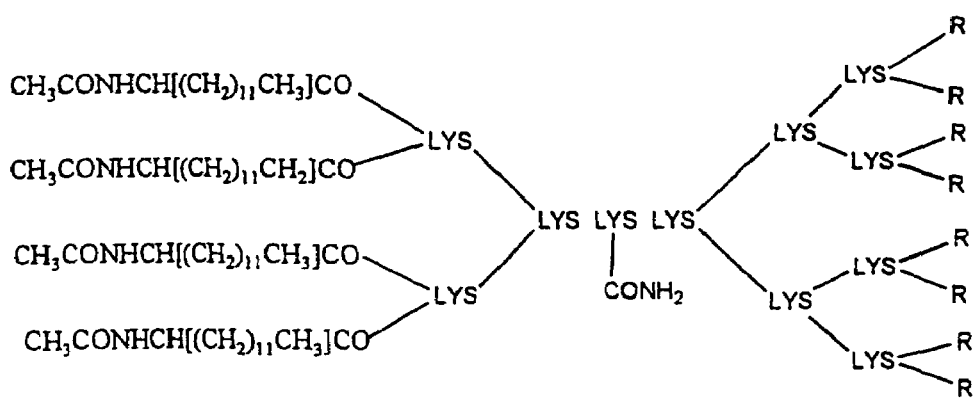

See FIGS. 1–3 for an explanation of compound structures, 2.5 µg vector DNA per plate with (a) 10 µg, (b) 5 µg and (c) 2.5 µg dendrimer compounds. Compounds 2a and 2b were not used for transfections since they were poorly soluble.

EXAMPLE 4

Oligonucleotide Delivery to Cells In Vitro

To determine the efficacy of the dendrimers (1a and 1b) in oligonucleotide delivery, 1 µg of a fluorescein-labelled oligonucleotide derived from human Factor VIII cDNA [AGT GCC ACC AGA AGA TAC](Seq. ID No. 4) was incubated with 2.5 µg of dendrimer for 30 mins at room temperature as described above. Oligo-dendrimer complexes were added to COS-7 cells previously grown on Thermanox coverslips (Nunc) in complete DMEM (as in Example 2.3). After 12–24 hrs, the cells were washed with PBS, fixed with 3.7% paraformaldehyde and permeabilised with 0.05% saponin. They were then processed for fluorescence microscopy. As a control for dendrimer-mediated delivery, free uncomplexed (fluorescein labelled) oligonucleotide was diluted in Optimem I and added directly to the cells.

Fluorescence microscopy showed a punctate pattern involving nuclei that had transported the oligonucleotide. In contrast, there was no significant nuclear localization by the free oligonucleotide. It thus appeared that the dendrimers protected the oligonucleotide from nuclease degradation, and serum factors, and efficiently transported it to the nucleus. Up to 50–80% of the cells showed nuclear fluorescence, per field. Although the free oligonucleotide was probably endocytosed as well, it was not sufficiently targeted to the nucleus, and was probably degraded due to lack of protection from nuclease attack. Hence, the dendrimers are sufficient to facilitate both oligonucleotide binding and delivery to the nucleus.

EXAMPLE 5

In Vivo Delivery in Mice

To assess the ability of the dendrimers 1a or 1b to delivery DNA in vivo, a secreted alkaline phosphatase vector (pSEAP control, Clontech) was used. 100 µg of plasmid was complexed with 200 µg of dendrimers 1a or 1b in a total volume of 300 µl in normal saline. After 30 mins, the complex was injected in vitro via the tail vein. Plasma was obtained from heparinized blood bled from the mice after 7 days. SEAP activity was determined using the Great EscAoe SEAP chemiluminescent assay system (Clontech) as suggested, and measured in an LKB Wallac luminometer.

Background endogenous alkaline phosphatase activity was eliminated by pretreatment of the plasma at 65° C. and incubation with the inhibitor L-homoarginine, since SEAP is resistant to these treatments. Chemiluminescent assays of SEAP activity in mouse plasma showed some expression of this reporter (FIG. 6) though at a low level. This low level may be due to a plethora of variables including a low targeting of vector to the cells etc.

EXAMPLE 6

Transient Transfection of HEK 293 Cells Using Dendrimers

Human Embryonic Kidney (HEK) 293 cells were sub-cultured onto poly-L-lysine coated 35 mm petri dishes such that 24 h later the cells were still sub-confluent. Culture media was replaced on the morning of the transfection procedure. Cells were returned to the $CO_2$—incubator (7.5% $CO_2$/95% air) for 3 h.

Compound 1a was incubated with a $GABA_A$ receptor α1 subunit cDNA-pCDM8 (Mammalian cell expression vector Thompson C. L. et al Neuroscience Let. 144 53–56 (1992)) construct ($F_c$2 µg/ml) in DMEM at weight ratios of 1:1, 10:1 and 100:1 (1a:α1 cDNA) for 30 minutes prior to transfection.

Cells were washed 3× with serum-free DMEM prior to application of compound 1a/$GABA_A$ receptor α subunit cDNA-vector (1ml/dish). Dishes were returned to the incubator (37° C.) for 5 h. Media was then supplemented with DMEM/10% FCS (1 ml/dish), returned to the incubator for 24 h.

Cells were also transfected with $GABA_A$ receptor α1 subunit cDNA- vector by the calcium phosphate precipitation method to act as positive controls.

The following regimes were adopted:—
i 4 dishes untreated (negative controls).
ii 4 dishes transfected by the calcium phosphate precipitation method (positive controls).
iii 4 dishes treated with α1 cDNA vector (2 µg/ml) alone.
iv 4 dishes treated with compound 1a (20 µg/ml) alone.
v 4 dishes treated with compound 1a (200 µg/ml) alone.
vi 4 dishes treated with compound 1a/α1 cDNA- vector (2 µg:2 µg/ml)
vii 4 dishes treated with compound 1a/α1 cDNA- vector (20 µg:2 µg/ml)

viii 4 dishes treated with compound 1a/α1 cDNA- vector (200 µg:2 µg/ml)

24 h later the cells were washed 3× with phosphate-buffered saline and then fixed with methanol (−20° C., 25 min, 2 dishes from each regime) or 4% parafarmaldehyde (room temp., 15 min, 2 dishes from each regime). The cells were then processed for GABA$_A$ receptor α1 subunit-like immunoreactivity according to Thompson et al. Immunoreactivity was detected by diaminobenzidine staining and visualised under the light microscope.

Results

Immunoreactivity was not detected in negative controls, in cells treated with GABA$_A$ receptor α1 subunit-vector alone or cells exposed to compound 1a(2–200 µg/ml) alone.

Neither was α1 subunit-like immunoreactivity detected in cells treated with compound 1a cDNA-vector ratios of 1:1 or 100:1, indeed 200 g/ml compound 1a was deleterious to cell viability and resulted in cell ghosting characteristic of membrane permeabilisation.

Positive results were obtained by the calcium phosphate precipitation approach, with a transfection efficiency of approximately 5%. Methanol and paraformaldehyde fixed cells both being immunopositive.

Likewise cells treated with compound 1a α1 cDNA-vector (10:1) were also immunopositive when fixed by methanol or paraformaldehyde approaches (n=4). Transfection efficiency under these conditions was good, if not better (5–10%), than calcium phosphate precipitation which is the universally employed method of choice for the transfection of HEK-293 cells.

Clearly, this carrier system can be used to deliver genetic material to the cell interior in a form that can be processed by the translation machinery.

EXAMPLE 7

Toxicity 7.1 Rat Erythrocyte Lysis Studies

Fresh blood was obtained from rats through cardiac puncture, collected in heparinised tubes and centrifuged at 1,000 g for 15 minutes at 4° C. The supernatant, was discarded, the volume was made up to 10 ml with chilled phosphate buffered saline (PBS). The suspension was centrifuged again and the PBS washing step was repeated twice. Finally, the supernatant was removed and the cell pellet resuspended up to 2% w/v in chilled PBS. 100 µl of samples of dendrimers 4a–c and 1a–c of different dilutions were added in flat bottomed Elisa plate. 1% w/v of Triton X 100 was used as the control (100% lysis). 100 µl of erythrocyte suspension was added and incubated for 1 h, 5 h and 24 hrs. At different time intervals these plates were removed and the suspensions centrifuged. 100 µl of the supernatant was removed and placed into fresh Elisa plate and the absorbance was measured at 545 nm with PBS as blank. The % population lysis was calculated by using the formula Percentage population lysis=(Absorbance/control (triton) absorbance) 100.

Results

The toxicity of the dendrimers were compared with linear polylysine of two different molecular weights (34,000 and 1000–4000). Triton X100 was used as positive control. The higher M.W. polylysine had a concentration independent toxicity 35.7% to 54.2% of percent population lysis was observed between the concentrations 1 µg/ml to 30 µg/ml. The lower M.W. polylysine was found to be almost non-toxic.

Red blood cell lysis studies indicated that dendrimers 1a–c were non toxic at the low concentration of 1 µg/ml after 24 hrs where as at higher concentrations (above 20 µg/ml) these compounds were toxic even after one hour incubation. All dendrimers had concentration dependent toxicity.

The toxicity studies of compounds 4a–c showed that the toxicity is dependent on the ratio of the lipophilic groups to the number of amino groups attached to the molecule. Compound 49 which contained 8 amino groups found to be less toxic than similar compounds having 16 and 32 amino groups 4b and 4c were less toxic than compounds 1a to c. This indicates that although compounds 4a–c were bulkier, the position of attachment of lipo amino acid makes them less toxic than compounds 1a–c.

7.2 Cytotoxicity of Dendrimer/Plasmid Complexes

Observations were made of the cell growth in Example 3. No significant differences in the cytotoxicity of the dendrimer vectors could be observed, using the criteria (1) cell detachment, (2) trypan blue exclusion and (3) glucose uptake. After a further 24 hours, the number of viable cells were determined using trypan blue exclusion. A duplicate experiment determined the percentage of transfected cells expressing β-galactosidase form pSVβgal by cleavage of X-gal substrate by the enzyme to give blue coloured cells. Results indicated that the number of transfected cells is maximal when the charge ratio is about 0.3 to 0.7. This range also corresponded to maximal cell survival. FIG. 7 shows the relationship between cell survival and transfection (1a was at 0.09 µg/µl and DNA concentration was varied)

This indicates that both uncomplexed compound and DNA are harmful to cells at high concentrations, but at an optimum ratio, the complex between the two reduces potential toxicity, and enhances transfection.

EXAMPLE 8

Effect of Charge Ratio on Transfection Rates for Compound 1a Complexes

The transfection properties of 1a were examined. BHK-21 cells were cultured to about 50–60% of confluence. A series of concentrations of Compound 1a and the DNA plasmid pSVβgal (which encodes for beta-galactosidase) were prepared so that the charge ratios of negative to positive charges of DNA to dendrimer ranged from 0.1 to 1 in serum free GMEM. The samples were left to incubate with BHK-21 cells for four hours after which the complex was removed and replaced with serum containing GMEM.

EXAMPLE 9

Effect of Complexing Polypeptides with DNA on RBC Lysis

The effects of various dendritic polypeptides alone and in combination with DNA (the plasmid used in Example 8) in a red blood cell lysis test as described in example 7 above, were investigated.

Rat red blood cells were obtained by centrifugation of complete blood. A 2% suspension of cells was made in phosphate buffered saline. For each dendrimer compound tested (compounds 1a, 1b and 1c), 100 µl of cell suspension was incubated with 100 µl of either compound alone or complexed with pSVβgal plasmid in a 96 well plate for 1 hour at 37° C. The lysate supernatant was recovered by centrifugation and the absorbance measured at 540 nm. (Concentration of pSVβgal was 0.0125 µg/µl).

The results (in FIG. 8) show that for compounds 1a and 1b, the complexing to DNA reduces levels of erythrocyte lysis.

EXAMPLE 10

Cell Toxicity and Transfection Rates for Compound 1b-DNA Complexes

In this example the effect of varying the ratio of dendrimer to DNA is investigated for Compound 1b, on cell toxicity and transfection. The plasmid pSVβgal is used in BHK21 cells. The transfection rate is determined using the synthetic chromogenic beta-galactosidase substrate Xgal. Cell survival is determined using the MTT test.

Compound 1b and complexes of 1b/pSVβgal were diluted in 140 µl of phosphate buffer. 140 µl of serum free GMEM was added and mixtures incubated on BHK-21 cells at 50–60% confluence at 37° C. and 5% $CO_2$ for 2 hours on 24 well plates. The mixture was removed and replaced with 400 µl of serum containing media. After 24 hours, the cell survival was estimated by addition of 80 µl of 5 mg/ml solution of MTT. MTT-formazan was dissolved in 400 µl of isopropanol and the absorbance of MTT-formazan measured at 595 nm. (Concentration of pSVβgal was 0.028 µg/µl). The results are shown in FIG. 9.

A series of complexes of pSVβgal/compound 1b were made so that the ratio of negative to positive charges varied from 0.1 to 0.4 at various concentrations of pSVβgal and compound. These complexes were diluted in 35 µl of phosphate saline buffer. A further 35 µl of serum free GMEM was then added and the mixture incubated on BHK-21 cells at about 50–60% of confluence in a 96 well plate for 2 hours at 37° C. and 5% $CO_2$. The complexes were then removed and replaced with 100 µl of serum containing media. After a further 24 hours, the media was removed and the cells developed with X-gal solution to give blue colouration to pSVβgal transfected cells expressing β-galactosidase. The percentage cover of blue cells was then estimated under a microscope using a graticuled field of view. The results are shown in FIG. 10.

We conclude from Examples 8–10 that generally a complex of DNA and compound reduces potential toxicity associated with compound. At an optimum concentration of compound (36 ng/µl) and charge ratio (0.2), transfection is maximal. Both uncomplexed compound and pSVβgal alone are harmful to cells at high concentrations. The three different compounds have significantly different effects on cell viability.

EXAMPLE 11

FIX pDNA Complex, In Vitro Use

Materials and Methods:
Cells

All media and supplements with the exception of the antibiotic/mycotic solution were obtained from Gibco BRL, Paisley, UK. Hep G2 (ECACC cells Accession No. 85011430) were maintained in MEM supplemented with 1× non-essential amino acids, 10% FBS and 1× antibiotic/antimycotic solution (Sigma). All cells were kept at 37° C./5% $CO_2$ in a humidified incubator. COS7 cells were used as in Example 3.

Plasmid DNA And Cationic Dendrimers

The eukaryotic expression vector pCEP4 (Invitrogen) was modified at the multiple cloning site to include the human coagulation factor IX (FIX) cDNA including intron 1. (Kurachi, S. et al (1995) J. Biol.chem. 270, 5276–5281). Cationic dendrimers were used at 1 mg/ml in $dH_2O$. The type of dendrimer is specified in the results table.

Cell Transfection 24 hours prior to transfection, cells were seeded into 9.6 $cm^2$ 6 well multidishes (Life Technologies, UK) to reach 60–70% confluency at the time of transfection. The medium was replaced 2 hours before the addition of the complexes. The DNA/Cationic dendrimer complexes were prepared using 2.5 µg DNA/well diluted in 0.1 ml optiMEM™(Life Tech) or relevant solution (as specified in the results) and with the desired amount of cationic dendrimer diluted in 0.1 ml of the same solution. In some of the tests the complex was formed in the presence of 150mMNaCl/20mMNaHCO$_3$ which is believed to assist transfection (Escriuo, V, et al. Biochem. Biophys Acta 1368, 276–288 (1988)). In others chloroquine was added to the complexes before addition to the DNA at 100 µM. This is added as it is believed to improve trasfection for some systems (Luthman H; et al (1983) NUC. Acids Res. 11, 1295–1308. The type and amount of dendrimer is specified in the results table. The two were combined in a 12×75 mm Borex™ sterile culture tube, mixed gently by pipetting several times and left at room temperature for approximately 30 mins. 0.8 ml of complete medial (without 1× antibiotic/antimycotic solution), or media without FBS was then added before overlaying the mixture onto the cells and incubating at 37° C. for 2–5 hours. Following this incubation, 1 ml of complete media was added to each well and the cells incubated for 48 hours in total from the time of transfection.

hFIX ELISA 96 well Nunc Maxisorb™ microtitre plates (LifeTech.) were coated with rabbit anti-human FIX polyclonal antibodies (Dako A300) in dilution buffer (PBS, 0.01% Tween 20 v/v, 3% PEG 8000 w/v) by overnight incubation at 4° C. The plates were then washed 5 times with wash buffer (PBS, 0.01% Tween 20 v/v) and excess buffer removed. 0.1 ml of cell culture media from each sample was added to the plates in duplicate along with a range of standards (plasma sample from a pool of 20 individuals with no personal or familial history of thrombotic or haemostatic disorders), a test blank: Coag Trol P(Dade) diluted 1/100 and 1/200, a positive control from the normal 20 pool diluted 1/100 and 1/200 and a cell culture medium sample from untransfected cells. The plates were sealed and incubated with agitation at room temperature for 1 hour.

The plates were washed five times with wash buffer and excess buffer removed. 0 ml Rabbit anti-human FIX-horse radish peroxidase conjugated antibody in dilution buffer was added to each well which was then sealed and incubated with agitation for 1 hour at room temperature. The plate was washed 5 times with wash buffer (removing excess) and 0 ml of an o-phenylenediamine dihydrochloride solution (10 mg tablet dissolved in 15 mL 0.5 M sodium citrate, pH 5.0 with 7 µL 30% hydrogen peroxide added prior to use) added to each well followed by 10 minutes incubation at room temperature for each sample to effect colour development. The reaction was stopped by adding 0.1 ml of 1.5 M $H_2SO_4$ to each well at exactly the same time interval as the substrate was added followed by a brief shake of the plate.

The absorbance was measured at 492 nm with a Dynex MRX microplate reader (Billingshurst, UK). Factor IX levels were calculated by comparison with a standard curve of serial dilutions of FIX derived from the normal human plasma. The results are reported as ng FIX per ml cell culture medium.

Electron microscopy was used to observe the morphology of some of the complexes.

Results

The results for transfections of the pG2 and COS7 cells are shown in Table 2.

TABLE 2

| Dendrimer | Amount µg | Charge ratio Dendrimer:DNA | Additions | Cells | FIX ng/ml |
|---|---|---|---|---|---|
| 1b | 10 | 8.2:1 | — | HepG2 | 11.5 |
| 1b | 20 | 16.3:1 | — | HepG2 | 2.0 |
| 1b | 10 | 8.2:1 | MEM | HepG2 | 11.5 |
| 1b | 20 | 16.3:1 | MEM | HepG2 | 6.5 |
| 1b | 10 | 8.2:1 | HCO₃ | HepG2 | 16.0 |
| 1b | 20 | 16.3:1 | HCO₃ | HepG2 | 1.0 |
| 3a | 10 | 4.3:1 | — | HepG2 | 9.5 |
| 1d | 10 | 5.9:1 | — | HepG2 | 1.0 |
| 1b/1d | 9/1 | 4.4:1 | — | HepG2 | 3.5 |
| 1b/d | 5/5 | 5.1:1 | — | HepG2 | 5.0 |
| 1b/3a | 9/1 | 7.8:1 | — | HepG2 | 10.0 |
| 1b/3a | 5/5 | 6.2:1 | — | HepG2 | 3.0 |
| 1b | 10 | 8.2:1 | Chlor | HepG2 | 9.0 |
| Control | | | | HepG2 | 1.0 |
| 1b | 5 | 4.1:1 | — | COS7 | 12 |
| 1b | 5 | 4.1:1 | FBS | COS7 | 37 |
| 1b | 10 | 8.2:1 | — | COS7 | 10 |
| 1b | 10 | 8.2:1 | FBS | COS7 | 40 |
| 2b | 5 | 4.5:1 | — | COS7 | 3 |
| 2b | 5 | 4.5:1 | FBS | COS7 | 22 |
| 2b | 10 | 8.9:1 | — | COS7 | 19 |
| 2b | 10 | 8.9:1 | FBS | COS7 | 28 |
| 3a | 5 | 2.1:1 | — | COS7 | 1 |
| 3a | 5 | 2.1:1 | FBS | COS7 | 6.5 |
| 3a | 10 | 4.3:1 | — | COS7 | 11 |
| 3a | 10 | 4.3:1 | FBS | COS7 | 24 |
| Lipofectamine | 5 | NK | — | COS7 | 12 |
| | 5 | NK | FBS | COS7 | 25 |
| | 10 | NK | — | COS7 | 43 |
| | 10 | NK | FBS | COS7 | 22.5 |
| Control | 0 | N/A | — | COS7 | N/A |
| | 0 | N/A | FBS | COS7 | N/A |

The results indicate that the level and type of dendrimer has an effect on transfection efficiency. Charge ratios of dendrimer:DNA to higher than 10:1 seem to be undesirable.

The corresponding electron microscopy pictures show the size/morphology of the complexes when formed in various solutions. The absence or presence of serum appears to have the greatest effect on the morphology of the 150 mM NaCl/20 mMNaHCO₃ and the MEM preparations, with little effect on the Optimem formed complexes. It would suggest that the small (approx. 150 nm)/homogeneous particles show the highest levels of expression when used to transfect HepG2 cells.

The levels of transfection seem to be approaching those, which it repeated in vivo would translate to therapeutically useful levels of FIX expression, the levels approaching the in vitro levels seen by Lozier, J. N. et al, Hum. Gene Ther. (1997) 8:1481–1490.

EXAMPLE 12

In Vivo Distribution of hFIXpDNA and 3H-Dendrimer

Tritiated dendrimer synthesised as described in Example 1 above except 3H labelled BOC-lysine was prepared quantitatively from 3H-lysine purchased commercially based on the method of Keller et al Organ. Synth. 63, 160–170 (1985) (1a: Specific Activity 31Bq/ug @ 5 µg/µl in dH₂O) were made up to 1.2 µg/µl with 0.9% w/v sodium chloride BP. For each animal, complexes were formed at room temperature by adding 5 µg pCEP4hFIXint (as used in Example 11) in 100 µl 0.9% sodium chloride BP) dropwise to 100 µl dendrimer solution (dendrimer:DNA charge ratio about 4:1) with moderate vortexing. The complexes were then sonicated on ice with a hand-held probe at low power setting several times with three second pulses.

Male C57BL/6mice (8–10 weeks) were divided into two groups. The first group (n=8) were given approx. 150–200 µl of the complexes (exact dose determined by difference in weight of syringe pre/post injection) via tail vein injection. The second (n=4) were administered 150 µl of the complexes in a dosed food particle (isolation/observation confirmed ingestion of the food particle). At time-points 2 hours, 24 hours, 4 days, 7 days (group 1) and 24 hours, and 7 days (group 2) the mice were sacrificed and organs/fluids harvested. Blood and urine were collected when possible post mortem, the former in citrate tubes. Organs were weighed and immediately immersed in liquid nitrogen cooled isopentane to be kept at −80° C.

DNA and RNA was isolated from the samples using a modified protocol for the SV Total DNA Isolation System (Parts 1–6 of Promega, Technical Manual part TM048 (rev. 12/98) and step 3 onwards from Promega Abtes No 69 (http://www. Promega.com/pnotes/69/7542% 5F19/7542% 5F 19, html), "separate isolation of Genomic DNA and total RNA from single samples using the SV Total RNA isolation system by Paul Otto et al).

Organ samples for liquid scintillation counting (for detecting dendrimer) were processed as per "Packard Counting Solutions" protocol for samples <30 mg using Solvable (Packard) for all tissues except blood, urine and digestive tract tissues that were dissolved using Soluene-350 (Packard). The LSC cocktail used was Ultima Gold. Counting time was 10 minutes. Detection of episomal DNA was performed by PCR using primers that amplified a 460 bp section of the plasmid of the 3′ end of hFIX cDNA and the SV40 pA region (sense: CAGGGCCTCTCACTAACTAATCAC (sequence ID No. 5), (antisense: CAGCCGGATCATAATCAGCCATAC sequence ID No. 6)

Final reaction conditions were as follows (Promega reagents used throughout):

1×Thermophilic DNA Polymerase Buffer
1.5 mM MgCl₂
0.2 mM each dNTP
50 pmoles sense primer
50 pmoles antisense primer
1.25 U Taq DNA Polymerase
1–2 µl template DNA
The volume was made up to 50 µl with dH₂O
Thermal cycling parameters: 30 cycles of 30 seconds @ 94° C., 30 seconds @55° C., 30 seconds @ 72° C.

Amplification products were run on a 0.8% w/v agarose gel, developed with ethidium bromide and viewed under UV light.

Results

Table 3 shows the results of the investigations on the distribution of ³H dendrimer. The results are expressed as % of label found in the indicated organ for each animal. It appears that dendrimer is directed to the liver where the DNA is injected intravenously. Even for the early time oral delivered complex, there is delectable dendrimer in the liver. For FIX delivery it is desirable for the DNA to be delivered to the liver.

The results of the DNA detection show that, for the animals injected i.v. and sacrificed at 2 hours plasmid is found in all organs other than brain. After 24 hours there appears to be some DNA in liver, but we did not find a consistent pattern of distribution in other organs at this time. No DNA could be detected in any of the organs for the oral delivered complex.

It appears that the DNA is protected by the dendrimer for a limited period in the circulation and cells. It is possible, however that the DNA is, after that period being transcribed and translated in transfected cells. Further work is being done to identify transcribed mRNA and FIX protein.

EXAMPLE 13

Effect of pH on Complex Formation

The method of Example 2.2 was used to investigate whether the retardation of DNA electrophoresis is affected by pH. 1% agarose gels were loaded immediately after complex formation (using a range of charge ratios with dendrimer 1a and pSVβgal) and left to run for 2 hours. In one series the mobile phase reservoir was not stirred. In the other the mobile phase reservoir was stirred.

The pH affects dendrimer binding to DNA. Electrophoresis without stirring results in pH 11 at the negative terminal, pH 4 at the positive and a pH gradient in the gel. Thus at the loading wells the pH is very alkaline, the dendrimer does not aggregate the DNA and the DNA runs into the gel even for high (greater than 1) dendrimer:DNA charge ratios. But on the gel with stirring pH 7 to 8 is maintained throughout and the dendrimer/DNA complex remains in the well where the charge ratio is greater than 1.

Where the charge ratio is less than 1 the dendrimer retards some DNA transport, but uncomplexed DNA from such mixtures can be seen transported at the same rate as DNA to which no dendrimer is added.

TABLE 4

| | | % age Total Dose (or Activity as Bq/mg tissue or Bq/0.1 ml fluid sampled) | | | | | | | | |
|---|---|---|---|---|---|---|---|---|---|---|
| Animal no. | Time | Liver | Spleen | Heart | Lungs | Kidney | Brain | Muscle | Testes | Urine |
| i.v.1 | 2 hours | 10.35 | 1.00 | 0.22 | 0.47 | 0.34 | (4 dpm/mg) | n/a | (9 dpm/mg) | (21 Bq/0.1 ml) |
| i.v.2 | 2 hours | 2.07 | 0.30 | 0.06 | 0.13 | 0.48 | n/a | n/a | n/a | n/a |
| i.v.3 | 24 hours | 8.05 | 0.61 | 0.80 | n/a | 0.57 | n/a | n/a | n/a | 0.52 |
| i.v.4 | 24 hours | 0.71 | 0.07 | 4.89 | n/a | 1.63 | (11 dpm/mg) | n/a | (2 dpm/mg) | n/a |
| i.v.5 | 4 days | 6.58 | 0.18 | 1.48 | 0.95 | 0.21 | n/a | n/a | n/a | n/a |
| i.v.6 | 4 days | 39.68 | n/a | n/a | n/a | 13.51 | n/a | 0.03 | (45 dpm/mg) | 1.3 |
| i.v.7 | 7 days | 2.91 | 0.53 | 1.53 | n/a | 0.89 | n/a | n/a | n/a | n/a |
| i.v.8 | 7 days | 6.53 | 0.51 | n/a | 0.16 | 5.68 | n/a | n/a | (23 dpm/mg) | n/a |
| Oral9 | 24 hours | 3.70 | 0.16 | n/a | n/a | 0.52 | n/a | n/a | n/a | 0.48 |
| Oral10 | 24 hours | 1.84 | 0.13 | 0.53 | 0.78 | 0.29 | n/a | n/a | n/a | 0.75 |
| Oral11 | 7 days | n/a | n/a | n/a | n/a | n/a | n/a | n/a | n/a | n/a |
| Oral12 | 7 days | n/a | n/a | n/a | n/a | n/a | n/a | n/a | n/a | n/a |

The invention claimed is:

1. A complex comprising, in admixture, a cationic polymer compound and an oligo- or poly-nucleotide anionic active compound, characterised in that the polymer compound comprises a dendritic core having a) a focal group and b) at least one dendron having n levels of dendritically linked trifunctional monomer units where n is in the range 2 to 6 and $2^n$ terminal branches, cationic groups at at least 50% of said terminal branches of the at least one dendron, and an anchor moiety comprising at least two lipophilic $C_{6-24}$-alkyl, -alkenyl or -alkynyl groups covalently conjugated in the polymer compound.

2. A complex according to claim 1 in which the dendritically linked monomer units are amino acid units.

3. A complex according to claim 2 in which the amino acid units each have the formula I

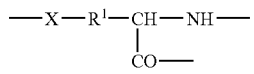

in which $R^1$ is $C_{1-6}$-alkanediyl; and
X is —O—, —NH, —S— or —CO—.

4. A complex according to claim 3 in which $R^1$ is linear $C_{2-4}$-alkanediyl.

5. A complex according to claim 3 in which X is —NH—.

6. A complex according to claim 1 in which the said anchor moiety is joined to said focal group.

7. A complex according to claim 6 in which the anchor group comprises lipidic amino acid units joined in series by peptide bonds.

8. A complex according to claim 7 in which each lipidic amino acid group has the formula II

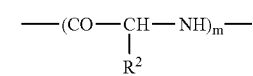

in which $R^2$ is $C_{6-24}$-alkyl, -alkenyl or -alkynyl; and
m is at least 2.

9. A complex according to claim 8 in which $R^2$-is $C_{8-16}$-alkyl and m is 3.

10. A complex according to claim 5 in which the anchor moiety is joined to the focal group, in which the anchor group comprises lipidic amino acid units joined in series by peptide bonds, each lipidic amino acid having the formula II

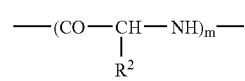

in which
$R^2$ is $C_{6-24}$-alkyl, -alkenyl or -alkynyl; and
m is at least 2.

11. A complex according to claim 10 in which $R^2$ is $C_{8-16}$-alkyl and m is 34.

12. A complex according to claim 1 in which the cationic polymer compound comprises further a second dendron of dendritically linked trifunctional monomer units, in which the anchor moiety comprises two or more lipophilic groups each joined to one of two or more terminal groups of the said second dendron.

13. A complex according to claim 12 in which each lipophilic group has the formula III

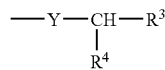

in which Y is —CO—, —NH—, —O— or —S—;
$R^3$ is an organic group containing at least one $C_{6-24}$-alkyl, -alkenyl or -alkynyl group; and
$R^4$ is hydrogen, amine, protected amine, blocked amine, hydroxyl, blocked hydroxyl, thiol, blocked thiol, carboxylic or blocked carboxylic, $C_{1-5}$-alkyl, -alkenyl or alkynyl group or is a group selected from the same groups as $R^3$.

14. A complex according to claim 13 in which
Y is —CO—;
$R^3$ is $C_{6-24}$ alkyl; and
$R^4$ is $NHCOCH_3$.

15. A complex according to claim 12 in which the number n of levels of dendritically linked units in the said at least one dendron is in the range 3 to 6.

16. A complex according to claim 12 in which the number n of levels of dendritically linked units in the said at least one dendron is in the range 3 to 6.

17. A complex according to claim 12 in which the number of levels of dendritically linked units in the second dendron is 2.

18. A complex comrising in admixture a cationic hydrophobised polypeptide compound and an oligo- or polynucleotide anionic active compound, characterised in that the polypeptide compound comprises a cationic polypeptide moiety formed from amino acid units having pendant amine groups, and an anchor moiety joined to the cationic polypeptide moiety through peptide bonds, the anchor moiety comprising at least two groups of the formula IV

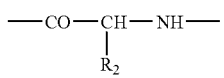

in which $R^2$ is a $C_{6-24}$-alkyl, -alkenyl or -alkynyl group.

19. A complex according to claim 18 in which the anchor is a group of formula II

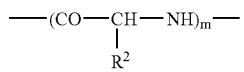

in which
$R^2$ is $C_{6-24}$-alkyl, -alkenyl or -alkynyl; and
m is at least 2.

20. A complex according to claim 19 in which $R^2$ is $C_{8-16}$-alkyl and m is 3.

21. A complex formed of an oligo- or polynucleotide and an anchored cationic polypeptide compound, in which the polypeptide compound comprises a core having at least one dendron of n levels of dendritically linked amino acid units of the formula I

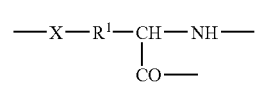

in which
$R^1$ is $C_{1-6}$-alkanediyl; and
X is —O—, —NH, —S— or —CO—
n is in the range 2 to 6; the polypeptide compound further having $2^n$ terminal branches
and having cationic groups at at least 50% of said terminal branches and further comprising an anchoring moiety conjugated to the polypeptide core.

22. A complex according to claim 21 in which the anchoring moiety is conjugated to the core through a peptide bond.

23. A complex according to claim 21 in which the oligo-or poly-nucleotide is counterionically bound to the cationic polypeptide.

24. A composition comprising a complex according to claim 1 and a carrier.

25. A composition comprising a complex according to claim 18 and a carrier.

26. A composition comprising a complex according to claim 21 and a carrier.

27. A pharmaceutical composition comprising a complex according to claim 1 and a pharmaceutically acceptable carrier.

28. A pharmaceutical composition comprising a complex according to claim 18 and a pharmaceutically acceptable carrier.

29. A pharmaceutical composition comprising a complex according to claim 21 and a pharmaceutically acceptable carrier.

30. A method in which a complex according to claim 1 is administered to an animal.

31. An in vitro method in which in a first step, a cell culture is transfected by a complex according to claim 1 and the culture is grown in a second step.

32. A method according to claim 31 in which the said oligo- or poly-nucleotide encodes a peptide or protein product and in which, in a third step, the cell culture is assayed for the said product, or the said product is isolated.

* * * * *